(12) United States Patent
Mashima et al.

(10) Patent No.: US 11,415,584 B2
(45) Date of Patent: Aug. 16, 2022

(54) BIOMARKERS, TEST METHOD, AND TEST KIT FOR PREDICTING THERAPEUTIC EFFECT OF ANTI-VEGFR-2 ANTIBODY DRUG

(71) Applicant: JAPANESE FOUNDATION FOR CANCER RESEARCH, Tokyo (JP)

(72) Inventors: Tetsuo Mashima, Tokyo (JP); Takeru Wakatsuki, Tokyo (JP); Hiroyuki Seimiya, Tokyo (JP); Kensei Yamaguchi, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 350 days.

(21) Appl. No.: 16/473,712

(22) PCT Filed: Dec. 27, 2017

(86) PCT No.: PCT/JP2017/046831
§ 371 (c)(1),
(2) Date: Aug. 12, 2019

(87) PCT Pub. No.: WO2018/124153
PCT Pub. Date: Jul. 5, 2018

(65) Prior Publication Data
US 2020/0355699 A1    Nov. 12, 2020

(30) Foreign Application Priority Data
Dec. 28, 2016   (JP) .............................. JP2016-255887

(51) Int. Cl.
*G01N 33/68*    (2006.01)

(52) U.S. Cl.
CPC ..... *G01N 33/6872* (2013.01); *G01N 2800/52* (2013.01)

(58) Field of Classification Search
CPC ..................... G01N 2800/52; G01N 33/6872
See application file for complete search history.

(56) References Cited

U.S. PATENT DOCUMENTS

| 9,469,876 B2 | 10/2016 | Kuslich et al. |
| 10,260,097 B2 | 4/2019 | Harkin et al. |
| 2016/0002732 A1 | 1/2016 | Harkin et al. |

FOREIGN PATENT DOCUMENTS

| JP | 2013-526852 | 6/2013 |
| JP | 2014-516552 | 7/2014 |
| JP | 2015-536667 | 12/2015 |

OTHER PUBLICATIONS

Hansjochen Wilke et al., "Ramucirumab plus paclitaxel versus placebo plus paclitaxel in patents with previously treated advanced gastric or gastro-oesophageal junction adenocarcinoma (RAINBOW): a double-blind, randomised phase 3 trial", Lancet Oncol, 2014; vol. 15 pp. 1224-1235; discussed in the specification.
Charles S. Fuchs et al., "Ramucirumab monotherapy for previously treated advanced gastric or gastro-pesophageal junction adenocarcinoma (REGARD): an international, randomised, multicentre, placebo-controlled, phase 3 trial", Lancet, 2014, vol. 383, pp. 31-39; discussed in the specification.
E. Van Custem et al., "Biomarker analyses of second-line ramucirumab in patents with advanced gastric cancer from RAINBOW, a global, randomized, double-blind, phase 3 study", Annals of Oncology, 2016, vol. 27 (Supplement 2): i118-ii128; discussed in the specification.
Charles S. Fuchs et al., "Biomarker analyses in REGARD gastric/GEJ carcinoma patients treated with VEGFR2-targeted antibody ramucirumab", British Journal of Cancer, 2016, vol. 115, pp. 974-982; discussed in the specification.
Andrew X. Zhu et al. "A Phase II and Biomarker Study of Ramucirumab, a Human Monoclonal Antibody Targeting the VEGF Receptor-2, as First-Line Monotherapy in Patients with Advanced Hepatocellular Cancer", Clinical Cancer Research, 2013, vol. 19, pp. 6614-6623; discussed in the specification.
Atsushi Ohtsu et al., "Bevacizumab in Combination With Chemotherapy as First-Line Therapy in Advanced Gastric Cancer: A Randomized, Double-Blind, Placebo-Controlled Phase III Study", Journal of Clinical Oncology, Oct. 20, 2011, vol. 29, No. 30, pp. 3968-3976; discussed in the specification.
English translation of International Preliminary Report on Patentability dated Jul. 2, 2019 (Jul. 2, 2019), Application No. PCT/JP2017/046831, 6 pages.
Ryoji Ichijima et al., "A human monoclonal antibody VEGER-2 antagonist ramucirumab (Cyramza) Clinical Gastroenterology", 2016, vol. 31, No. 1, English translation of introduction and conclusion included, 10 pages; cited in the International Preliminary Report on Patentability.

*Primary Examiner* — Ruixiang Li
(74) *Attorney, Agent, or Firm* — Rankin, Hill & Clark LLP (57) ABSTRACT

The therapeutic effect of and/or prognosis after administration of an anti-VEGFR-2 antibody drug, in particular, ramucirumab can be predicted by measuring VEGF-A, VEGF-D, sVEGFR-2, SDF-1α, and/or cNRP1. Provided is a biomarker for predicting the effect of administration of the anti-VEGFR-2 antibody drug, in particular, ramucirumab, and a test method and a test kit using the marker.

4 Claims, 6 Drawing Sheets

Figure 4
VEGF-A D8

Figure 5
VEGF-D D8

Figure 6
VEGF-A low & VEGF-D high vs Others

BIOMARKERS, TEST METHOD, AND TEST KIT FOR PREDICTING THERAPEUTIC EFFECT OF ANTI-VEGFR-2 ANTIBODY DRUG

TECHNICAL FIELD

The present invention relates to a marker for predicting therapeutic effect of anti-VEGFR-2 (vascular endothelial growth factor receptor-2) antibody drug and a test method and a test kit for predicting the therapeutic effect.

BACKGROUND ART

When cancer grows and metastasizes, generated are, as nutrient supply passages so as to maintain its proliferation, blood vessels for nutrients, what is called angiogenesis. Examples of an angiogenesis-inducing factor include vascular endothelial growth factors (VEGFs). VEGFR, a VEGF receptor, is a kind of receptor tyrosine kinase and, with its ligand VEGF, plays an important role in angiogenesis involving, for instance, proliferation of vascular endothelial cells and facilitation of their migration. The VEGFR family has been known to include soluble VEGFRs in addition to three members: VEGFR-1, VEGFR-2, and VEGFR-3. The VEGFR family has a similar structure and has homology to molecules such as platelet-derived growth factor (PDGF) receptor and stem cell factor receptor (SCFR, c-kit).

There is 43% homology between VEGFR-1 and VEGFR-2, and a kinase sequence inserted in their intracellular tyrosine kinase domain is most preserved. The binding of VEGFR-2 to its ligand is weaker than that of VEGFR-1. However, the tyrosine kinase activity of VEGFR-2 is strong, so that VEGFR-2 contributes largely to overall intracellular signal transduction and thus seems to largely participate in an angiogenic process. VEGFR-2 can bind to VEGF-A, C, D, and E and is a receptor, among three VEGFR members, that is considered to be most closely related to tumor angiogenesis induced by the VEGFs.

There has been progress to develop antibody therapeutics against VEGFR-2, which exerts a critical effect on angiogenesis involving cancer proliferation and metastasis. Ramucirumab (trade name "Cyramza"; manufactured by Eli Lilly and Company), a representative antibody drug, is a human monoclonal antibody which is a recombinant human immunoglobulin G1 (IgG1$^b$) against VEGFR-2.

Ramucirumab specifically binds to VEGFR-2, thereby inhibiting the binding of VEGFR-2 to its ligand VEGFs: VEGF-A, VEGF-C, and VEGF-D and thus inhibiting activation of VEGFR-2 and its downstream signal transduction pathway. As a result, proliferation and migration of vascular endothelial cells are inhibited, so that the resulting tumor angiogenesis is inhibited and an anti-tumor effect is thus exerted.

In commonly diagnosed several cancer types including gastric cancer, lung cancer, and colorectal cancer, the interaction between VEGFR-2 and its ligands is shown to cause tumor angiogenesis. Accordingly, ramucirumab has been approved in Japan as a drug for unresectable, recurrent/advanced gastric cancer, colon/rectal cancer, or non-small-cell lung cancer.

Among them, gastric cancer is most commonly diagnosed cancer and the second leading cause of death in Japan; and the number of patients with the cancer is very large. Of the unresectable, recurrent/advanced gastric cancer, the median survival time is 13 to 14 months and the prognosis is still poor. Thus, a suitable therapeutic drug and a therapeutic protocol have been sought.

In an international phase III clinical trial (RAINBOW trial), compared were gastric cancer-treated case subjects who received ramucirumab in combination with paclitaxel and who received placebo in combination with paclitaxel. Then, dosing of ramucirumab in combination with paclitaxel was found to significantly prolong overall survival (Non Patent Literature 1). In addition, in an international phase III clinical trial (REGARD trial), when compared with the placebo administration group, the ramucirumab monotherapy group was found to have an effect of significantly prolonging overall survival (Non Patent Literature 2). Thus, ramucirumab has been a major option for unresectable, recurrent/advanced gastric cancer therapy.

While ramucirumab is found to have efficacy on gastric cancer with less side effects in many patients, ramucirumab produces less therapeutic effect in some patients. If therapeutic effect can be predicted before initiation of therapy or in the early phase after initiation of therapy of such patients with less therapeutic benefit, alternative therapy may be implemented, without any useless therapy, on the patients from whom therapeutic benefit cannot be expected. This urges development of a suitable potent biomarker for predicting the above therapeutic effect from the viewpoint of appropriate drug use.

For prediction of the therapeutic effect of ramucirumab, molecules mainly participating in tumor angiogenesis through a VEGFR-2 signal transduction pathway were analyzed, including VEGF-C, VEGF-D, and soluble VEGFRs such as sVEGFR-1 (soluble VEGFR-1) and sVEGFR-2, and placental growth factor (PlGF), which is a growth factor member of the VEGF family. Reports (Non Patent Literatures 3 and 4) show the results indicating no association with any of them. According to the results of analyzing a cancerous tissue by tissue immunostaining, a group of expressing a high level of VEGFR-2 in endothelial cells tends to have a shorter progression-free survival (PFS) than a group of expressing a low level of VEGFR-2 in endothelial cells. Until now, no results have been obtained which provide prediction of prognosis after therapy or exhibit therapeutic effect. So, a marker for predicting therapeutic effect of ramucirumab has been sought. Nevertheless, there has been no currently approved biomarker for predicting the therapeutic effect.

Provided that although not specific to anti-VEGFR-2 antibody therapeutics, some methods for predicting therapeutic effect of each angiogenesis inhibitor including ramucirumab have been disclosed. Patent Literatures 1 and 2 each disclose a method for predicting a patient's response to an anti-angiogenesis drug. These methods are to determine, from the expression signature of total RNA from a patient's cancerous tissue, whether or not the patient responds to the anti-angiogenesis drug. Examples of the anti-angiogenesis drug include, in addition to ramucirumab, drugs such as bevacizumab (an anti-VEGF antibody drug), imatinib (a multiple tyrosine kinase inhibitor), gefitinib (an EGFR tyrosine kinase inhibitor), and erlotinib (an EGFR tyrosine kinase inhibitor), which are compounds with different action points. Consequently, the markers disclosed in these literatures cannot be used to specificity predict therapeutic effect of ramucirumab. Besides, in the methods disclosed in Patent Literatures 1 and 2, it is necessary to analyze total RNA of a cancerous tissue. When unresectable, recurrent gastric cancer is a target, a clinical sample can generally be hard to obtain by biopsy. The method described in Patent Literature 1 or 2 may thus not be used to actually carry out the analysis.

CITATION LIST

Non Patent Literature

Non Patent Literature 1: Wilke, H. et al., 2014, Lancet Oncol., Vol.15, p.1224-1235.
Non Patent Literature 2: Fuchs, C. S. et al., 2014, Lancet, Vol.383, p.31-39.
Non Patent Literature 3: Van Cutsem, E. et al., 2016, Ann. Oncol. Vol. 27(Issue suppl_2)ii120
Non Patent Literature 4: Fuchs, C. S. et al., 2016, Br. J. Cancer, Vol.115, p.974-982.
Non Patent Literature 5: Zhu, A. X, et al., 2013, Clin Cancer Research, Vol 19, p6614-6623.
Non Patent Literature 6: Ohtsu, A. et al., 2011, J. Clin. Oncol., Vol.29, p.3968-3976.

Patent Literature

Patent Literature 1: National Publication of International Patent Application No. 2014-516552
Patent Literature 2: National Publication of International Patent Application No. 2015-536667

SUMMARY OF INVENTION

Technical Problem

It is an object of the present invention to reveal a biomarker for predicting therapeutic effect of anti-VEGFR-2 antibody drug, in particular, ramucirumab, thereby assisting a test and therapy in clinical practice. If how each patient responds to anti-VEGFR-2 antibody drug is determined before initiation of therapy or in the early phase after initiation of therapy, it is possible to select a suitable therapy in which the anti-VEGFR-2 antibody drug is administered to only patients from whom the therapeutic benefit can be expected while avoiding useless therapy of patients from whom the therapeutic benefit cannot be expected. The purpose of the present invention is to provide a test method for determining a proper therapy when anti-VEGFR-2 antibody drug is applied.

As described above, use of a cancerous tissue as a sample is currently disclosed in a method of testing a response to an anti-angiogenesis drug. However, when recurrent/advanced cancer is a subject, it is often difficult in clinical practice to obtain a cancerous tissue by biopsy. Thus, conventional techniques using a cancerous tissue are not applicable. This urges a new test technology. The object of the present invention is to search a biomarker in a blood sample and then to develop a test method using the marker. Another purpose is to provide a test kit using the marker.

Solution to Problem

The present invention relates to a biomarker, a test method, and a test kit for predicting therapeutic effect of and predicting prognosis after therapy with anti-VEGFR-2 antibody drug, in particular, ramucirumab.

(1) A test method for predicting therapeutic efficacy of and/or predicting prognosis for administration of an anti-VEGFR-2 antibody drug, comprising measuring concentrations of VEGF-A in samples collected from a patient before initiation of therapy and in an early phase after the initiation of therapy.

(2) The test method according to (1), wherein a concentration of at least one of VEGF-D, sVEGFR-2, SDF-1α, and cNRP1 is further measured.

(3) The test method according to (2), where the concentrations of VEGF-A and VEGF-D are measured.

(4) The test method according to any one of (1) to (3), wherein the anti-VEGFR-2 antibody drug is ramucirumab.

(5) The test method according to any one of (1) to (4), wherein each of the samples is blood, plasma, or serum.

(6) A test kit for predicting therapeutic efficacy of and/or predicting prognosis for administration of an anti-VEGFR-2 antibody drug, comprising a reagent for measuring a concentration of VEGF-A in a patient sample.

(7) The test kit according to (6), further comprising a reagent for measuring a concentration of at least one of VEGF-D, sVEGFR-2, SDF-1α, and cNRP1.

(8) The test kit according to (7), wherein the reagent for measuring concentrations of VEGF-A and VEGF-D is comprised.

(9) The test kit according to any one of (6) to (8), wherein the anti-VEGFR-2 antibody drug is ramucirumab.

(10) A biomarker for predicting therapeutic efficacy of and/or predicting prognosis for administration of an anti-VEGFR-2 antibody drug, wherein the biomarker is any one of VEGF-A, VEGF-D, sVEGFR-2, SDF-1α, and cNRP1.

(11) The biomarker according to (10), wherein the anti-VEGFR-2 antibody drug is ramucirumab.

The present invention can help develop a therapeutic protocol in clinical practice because biomarkers have been obtained which can predict therapeutic effect of anti-VEGFR-2 antibody drug, in particular, ramucirumab. Specifically, it is possible to predict therapeutic effect of and prognosis after therapy with ramucirumab during the early phase stage after initiation of therapy. As a result, it is possible to provide information that helps determine whether or not ramucirumab should be administered.

DESCRIPTION OF EMBODIMENTS

As used herein, prognosis predictors or therapeutic effect predictors are defined as follows. Generally speaking, the prognosis predictors each refer to a factor that affects prognosis of a case regardless of the kind of therapy, and the prognosis prediction can be estimated by the Kaplan-Meier method. In the Kaplan-Meier method, every study subject is ordered ascending according to the time of death or discontinuation; the survival is calculated whenever the death occurs; and a step-like graph curve is plotted to estimate the survival. For instance, plotted are Kaplan-Meier curves between two groups: a group in which the level of a factor to be evaluated is high and a group in which the level is low. A clear difference between the two groups indicates that the survival is changed in response to the existing level of the factor evaluated. As a result, such an evaluated factor can be defined as a prognosis predictor that affects the prognosis. In addition, the therapeutic effect predictors each refer to a factor associated with therapeutic effect only when a specific drug is used, and provide important information on a therapeutic strategy when therapy with a molecular target drug is initiated.

Biomarkers disclosed herein may be used singly or may be used in combination. A combination of the markers allows for more accurate therapeutic effect prediction and prognosis prediction.

As described above, in recurrent/advanced cancer, it is difficult in clinical practice to obtain a cancerous tissue by biopsy. Thus, as used herein, the prognosis predictors and the therapeutic effect predictors are each specified as a blood biomarker. Each plasma sample is used as a sample in the Examples, but blood or serum other than the plasma sample may also be used. If blood, plasma, or serum is used, not only a test can be conducted by obtaining a sample from a patient even with unresectable, recurrent/advanced cancer, but also the patient's physical burden is small. Further, the samples can be collected before initiation of therapy, in the early phase after initiation of therapy, and when pathological conditions are changed, thereby providing more accurate test results.

In the present embodiment, gastric cancer is analyzed as a target. However, the present embodiment is applicable to gastric cancer, as well as colon/rectal cancer and non-small-cell lung cancer, which are targets for therapy with ramucirumab, and also liver cancer and other cancers, which are expected to be targets for therapy with ramucirumab in the future.

In addition, the present embodiment is not limited to ramucirumab and is widely applicable to VEGFR-2-targeting antibody drugs that are considered to exert a similar mechanism of action. Further, the present invention may be used to predict therapeutic effect of a VEGFR-2-targeting low-molecular-weight compound that shares a mechanism of action with the above antibody drugs, to predict prognosis after therapy thereof, and to develop a therapeutic protocol therewith.

Meanwhile, in the following Examples, each sample immediately before initiation of therapy is used as a baseline sample; and each sample at day 8 after initial dosing of ramucirumab is used as a sample obtained during the early phase after initiation of therapy. Provided that the sample in the early phase after initiation of therapy is not limited to a sample at day 8 after initial dosing of ramucirumab. Here, each sample obtained between day 4 and day 10 should exhibit substantially the same tendency. Accordingly, each sample obtained during this period may be used for analysis.

It is needless to say that any assay can produce substantially the same results indicating that each biomarker is associated with prognosis after and therapeutic effect of therapy with ramucirumab as shown in the following Examples. Thus, ELISA was used herein to examine patient samples. However, any kinds of assay are acceptable as long as the protein level of each biomarker in the sample can be measured. Because the assay sensitivity is high and a test is relatively simple, it is preferable to carry out immunoassay measurement. Examples of the immunoassay include, in addition to ELISA, radioimmunoassay (RIA), fluoroimmunoassay (FIA), fluorescence polarization immunoassay (FPIA), and chemiluminescent immunoassay (CLIA). Here, any of the above assays may be used. In addition, any forms of test device are applicable, including sample tubes, microtiter plates, microarrays, and MEMS (Micro Electro Mechanical Systems) chips. However, individual values such as a cut-off value and a median somewhat vary depending on a kit used and/or the number of patients, etc. Due to this, the individual numerical values such as a cut-off value may be individually determined by using a specific kit while the number of members of a population is increased.

A kit according to the present embodiment may include an antibody for detecting each biomarker found herein, such as VEGF-A, VEGF-D, SDF-1α, or cNRP1, and a reagent for detecting the antibody. Examples of the detection reagent include secondary antibodies, substrate agents, and labels (e.g., fluorescent dyes, enzymes). In addition, the above components may be optionally provided as a premix. The kit may further include a solid phase such as a microtiter plate, a reaction container, a washing solution, a buffer for diluting an antibody, a positive control, a negative control, and/or a written instruction describing a protocol.

Hereinafter, the present invention will be described specifically.

Subjects were patients, from whom an informed consent was obtained in The Cancer Institute Hospital Of JFCR, and subjects to be analyzed were selected according to the following criteria.

Selection Criteria

Cases satisfying the following conditions were enrolled.
1) Case histopathologically confirmed as unresectable, recurrent/advanced gastric cancer.
2) Case where as a second-line or later treatment, ramucirumab combined chemotherapy, ramucirumab monotherapy, or taxane (paclitaxel) monotherapy is implemented.
3) Case where an organ with a tumor is still functional.
4) Case without a complication such as severe bleeding, thrombosis, proteinuria, and hypertension.
5) Case with a written informed consent.

Exclusion Criteria
1) Case without a consent from the subject.
2) Case where enrollment in this study has been judged inappropriate.

Subjects for this analysis were 39 patients who were enrolled patients analyzed from January to November 2016 and whose clinical benefit was able to be determined by computed tomography (CT). Table 1 collectively provides 39 cases analyzed. Note that the numbers in parentheses at the Age row indicate the ages of the youngest and oldest patients analyzed.

TABLE 1

| Characteristics | N = 39 |
| --- | --- |
| Age | 68(35-83) |
| Gender M/F | 21/18 |
| PS 0/1/2/3 | 14/20/3/2 |
| Location GEJ/Distal St. | 5/34 |
| WHO differentiations | 8/31 |
| Diff./Undiff. | 9/30 |
| HER2 positive/negative | 22/17 |
| Previous gastrectomy Yes/No | 11/28 |
| Adj. Chemotherapy | 13/26 |
| TTP for 1st line CTx | 27/12 |
| ≥6 months/<6 months | 22/17 |
| Number of met. Site 0-2/≥3 | 22/17 |
| Peritoneal met. Yes/No | 7/32 |
| Present Ascites Yes/No | 22/17 |
| Liver met. Yes/No | 7/32 |

SDF-1α of each patient from before initiation of therapy to day 8 after the initiation of therapy to, depending on patients, a progressive disease stage. The analyzed markers had roughly two patterns: a pattern in which like VEGF-A, the concentration was low before initiation of therapy, but the blood concentration markedly increased during the early phase after the initiation of therapy; and a pattern in which like SDF-1α, there was no fixed tendency with respect to the concentration before initiation of therapy and a change after the initiation of therapy. Non Patent Literature 5 reports an increase in the levels of VEGF-A and PlGF at D8. This analysis confirmed substantially the consistent results of these proteins, indicating validity of this analysis system.

Table 2 shows a baseline of each measured protein (pre: the protein concentration before initiation of therapy), a difference between D8 and the baseline (D8 -pre), a median ratio (D8/pre), and quartiles.

TABLE 2

| Biomarker | m-Pre | quartile | m-D8-Pre | quartile | m-D8/Pre | quartile |
| --- | --- | --- | --- | --- | --- | --- |
| PlGF (pg/ml) | 9.2 | 4.8-13.5 | 124 | 101.3-217.1 | 18.1 | 11.2-26.4 |
| VEGF-A (pg/ml) | 18.4 | 3.0-40.7 | 250 | 182.5-444.2 | 19.3 | 8.0-103.3 |
| VEGF-C (pg/ml) | 996.7 | 683.3-1346.9 | 35 | −279.7-190.6 | 1 | 0.8-1.4 |
| VEGF-D (pg/ml) | 738.8 | 550.5-976.9 | 232.8 | 133.8-335.6 | 1.3 | 1.2-1.6 |
| sVEGFR1 (pg/ml) | 86.5 | 47.3-169.4 | −21.4 | −52.6-2.2 | 0.7 | 0.4-1.0 |
| sVEGFR2 (pg/ml) | 4710.7 | 3902.7-5309.8 | 491.3 | −6.4-1225.6 | 1.1 | 1.0-1.3 |
| cNRP (pg/ml) | 473824 | 324161.3-795363.5 | −89705 | −154320.0-−220.3 | 0.8 | 0.7-1.0 |
| SDF-1α (pg/ml) | 904.7 | 671.4-1544.2 | −1.8 | −314.9-446.6 | 1 | 0.6-1.6 |
| Ang-1 (pg/ml) | 1425.8 | 625.4-2591.1 | −13.9 | −1024.4-401.9 | 1 | 0.6-1.5 |

[Therapeutic Protocol]

Figure 1:
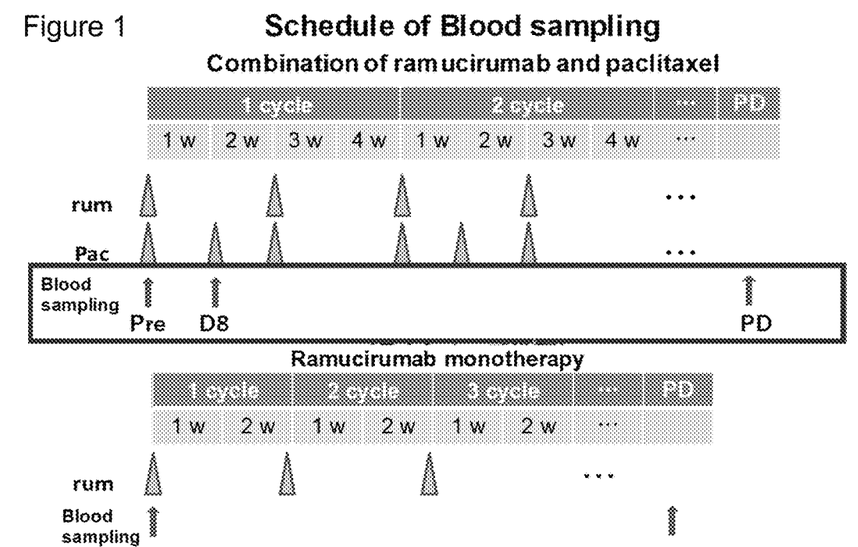
FIG. 1 is a diagram illustrating a schedule for drug administration and blood collection.

As illustrated in FIG. 1, ramucirumab (rum) in combination with paclitaxel (Pac), or ramucirumab alone was administrated. In the paclitaxel/ramucirumab combination therapy, 8 mg/kg of ramucirumab is administrated once every two weeks while paclitaxel is additionally administrated (at 80 mg/m$^2$ (body surface area) on day 1, day 8, and day 15 in one cycle defined as 4 weeks). In the case of ramucirumab monotherapy, 8 mg/kg of ramucirumab is administrated once every two weeks. The therapy continues until the primary disease progresses or a severe adverse event, in which dosage control is difficult, occurs.

[Test Method]

About 5 mL of blood is collected before initiation of initial therapy with ramucirumab, at day 8 after the initiation of initial therapy (hereinafter, sometimes referred to as D8), and in a progressive disease (PD) stage, and each plasma sample is separated therefrom and stored at −80° C. Each candidate cytokine was measured by ELISA.

VEGF-A, VEGF-C, VEGF-D, PlGF, SDF-1α, angiopoietin 1, sVEGFR-1, sVEGFR-2, and cNRP1 (circulating Neuropilin 1), which are known to participate in angiogenesis, were selected as analytes and were analyzed. The plasma concentration of each protein was measured by using a cytokine assay ELISA kit Quantikine (registered trademark; manufactured by R&D Systems, Inc.) to examine the progression-free survival, overall survival, partial response (PR), and severe adverse event incidences of each patient.

Figure 2:
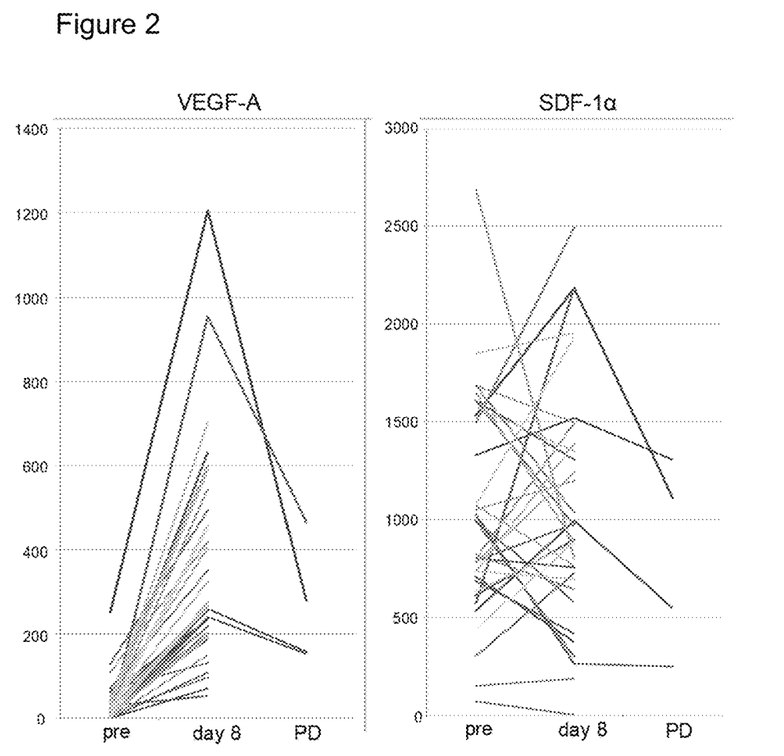
FIG. 2 is graphs showing typical behaviors of proteins analyzed.

FIG. 2 shows a typical pattern of change in the level of each analyte protein between before initiation of therapy and day 8 after the initiation of therapy. FIG. 2 is graphs showing the plasma concentration of VEGF-A or SDF-1α in each patient. Each line indicates the concentration of VEGF-A or It was observed that PlGF, VEGF-A, VEGF-D, and sVEGFR-2 were increased, from the baseline (Pre; before initiation of therapy), at day 8 (D8) after initiation of ramucirumab dosing. Meanwhile, it was observed that the concentration of each of sVEGFR-1 and cNRP1 was decreased from before the initiation of therapy. Regarding the other proteins, no clear tendency was found. Note that in the table, m represents a median; m-Pre indicates a median of levels before initiation of therapy (Pre); m-D8-Pre indicates a median of values obtained by subtracting each measured level before initiation of therapy from each measured level at day 8 (D8) after the initiation of ramucirumab dosing; and m-D8/Pre indicates a median of D8/Pre ratios.

A change in the blood concentration of each biomarker and the therapeutic effect were examined. Whether or not each protein, the level of which was found to change, was correlated with progression-free survival or overall survival was analyzed. The results demonstrated that expression of each of VEGF-A, VEGF-D, sVEGFR-2, SDF-1α, and cNRP1 was correlated with therapeutic effect and prognosis.

Figure 3:
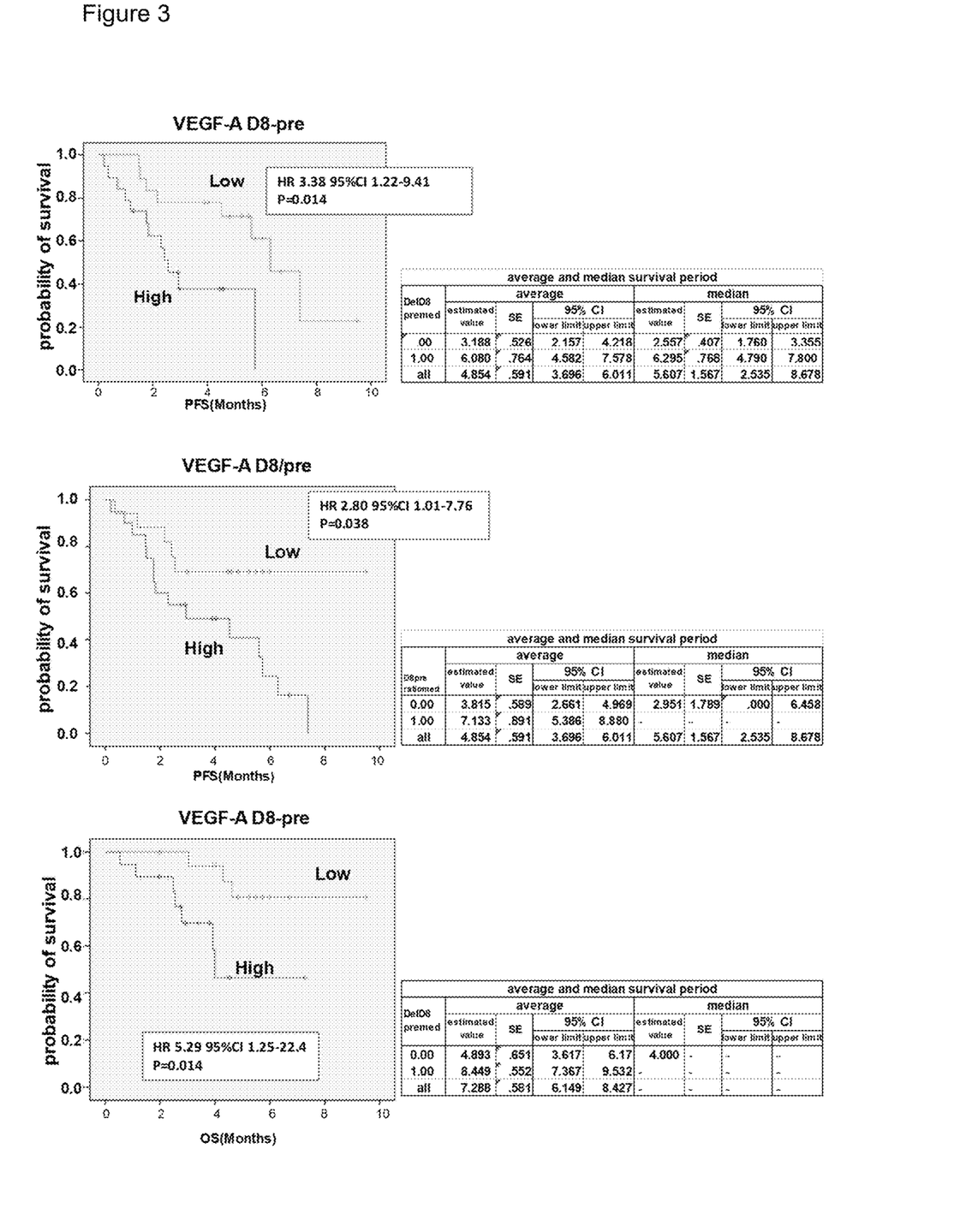
FIG. 3 is graphs and tables indicating that VEGF-A is correlated with PFS or overall survival (OS).

Regarding VEGF-A, when the difference between the baseline and D8 was higher than the median, namely when the D8 increase was higher, prognoses (PFS) were significantly poorer than otherwise (FIG. 3, upper panels). The PFS was 6.3 months in the group where the value obtained by subtracting the VEGF-A level before initiation of therapy from the VEGF-A level at D8 was lower than the median and 2.6 months in the group where the value was higher (the average of all the patients was 5.6 months), demonstrating a significant difference. The D8/baseline ratio likewise indicated that higher the ratio, the significantly poorer the therapeutic effect (FIG. 3, the middle panels). Here, this phenomenon, in which the level of VEGF-A is increased at D8, has not been observed in the cases of other drug administration and is thus a ramucirumab-specific change. VEGF-A is therefore a predictor for therapeutic effect of ramucirumab.

Further, similar results were obtained with respect to VEGF-A-related OS. Specifically, when the difference between the baseline and D8 was higher than the median, namely when the D8 increase was higher, overall survival (OS) was significantly poorer than that of the lower cases (FIG. 3, lower panels). Collectively, the above has demonstrated that VEGF-A is a useful biomarker for predicting therapeutic effect and prognosis.

Moreover, the follow-up period was prolonged for analysis (the average follow-up period was 9.8 months), and VEGF-A was further examined. Table 3 shows characteristics of 41 patients analyzed. Note that these patients overlap and include the patients of Table 1. Here, the numbers in parentheses at the Median Age row indicate the ages of the youngest and oldest patients analyzed. Otherwise, the numbers each represent a percentage (%) of patients included in the relevant group.

TABLE 3

| Characteristics | N = 41 (%) |
| --- | --- |
| Median age | 68(35-83) |
| Gender M/F | 22(54)/19(46) |
| PS 0/1/2/3 | 14(34)/20(49)/4(10)/3(7) |
| Location GEJ/Distal St. | 7(17)/34(83) |
| WHO differentiations Diff./Undiff./unknown | 9(22)/31(76)/1(2) |
| HER2 positive/negative | 10(24)/31(76) |
| Previous gastrectomy Yes/No | 22(54)/19(46) |
| Adj. Chemotherapy | 12(29)/29(71) |
| TTP for 1st line CTx ≥6 months/<6 months | 15(37)/26(63) |
| Number of met. Site 0-2/≥3 | 27(66)/14(34) |
| Peritoneal met. Yes/No | 23(56)/18(44) |
| Present Ascites Yes/No | 23(56)/18(44) |
| Liver met. Yes/No | 9(22)/32(78) |

Figure 4:
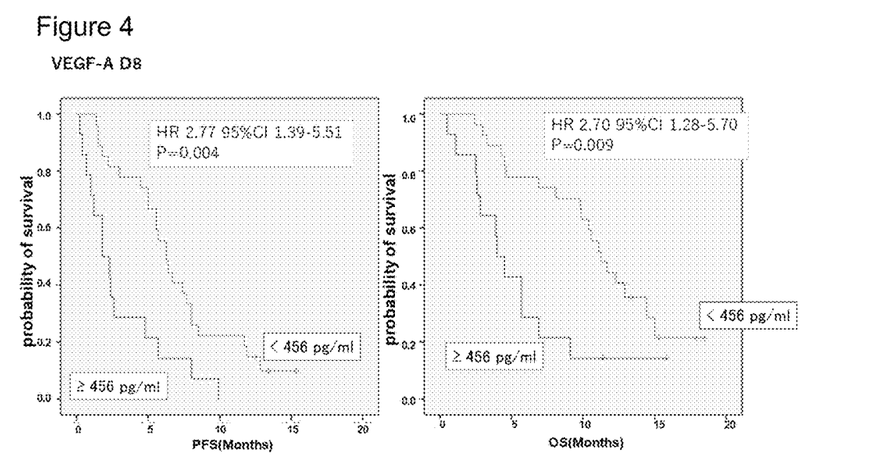
FIG. 4 is graphs indicating that VEGF-A is correlated with PFS or OS at day 8 after initiation of therapy with ramucirumab.

The VEGF-A level at day 8 after initiation of therapy with ramucirumab was strongly correlated with prognosis (FIG. 4). In the cases where the plasma VEGF-A level at day 8 after initiation of therapy was 456 pg/ml or higher, the median PFS was 1.8 months and 95% confidence interval (CI) was from 0.5 to 3.1 months. By contrast, in the cases where the level was less than 456 pg/ml, the median PFS was 6.3 months and 95% CI was from 5.1 to 7.5 months. In addition, in the cases where the VEGF-A level at day 8 after initiation of therapy was 456 pg/ml or higher, the median OS was 4.0 months and 95% CI was from 2.9 to 5.1 months. By contrast, in the cases where the level was less than 456 pg/ml, the median OS was 11.3 months and 95% CI was from 9.4 to 13.2 months.

Figure 5:
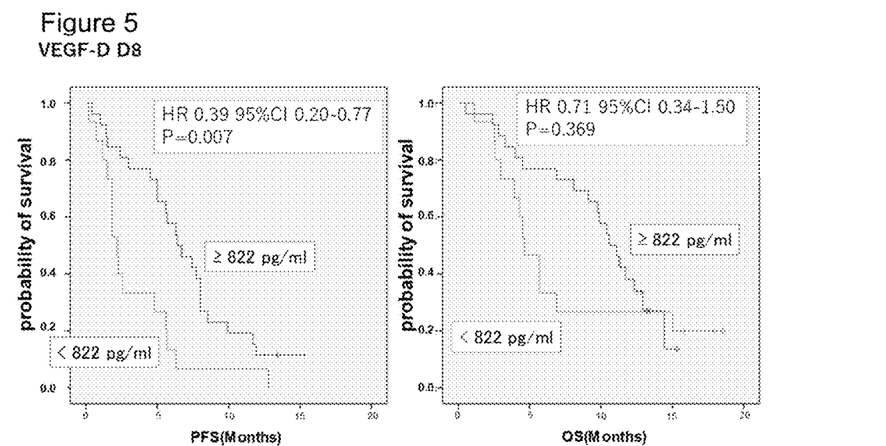
FIG. 5 is graphs indicating that VEGF-D is correlated with PFS or OS at day 8 after initiation of therapy with ramucirumab.

Further, the analysis results obtained by prolonging the follow-up period have revealed that in addition to VEGF-A, VEGF-D is an effective prognosis predictor or therapeutic effect predictor for therapy with ramucirumab. When the plasma VEGF-D level at day 8 after initiation of therapy with ramucirumab was high, prognosis was good (FIG. 5). In the cases where the VEGF-D level at day 8 after initiation of therapy was 822 pg/ml or higher, the median PFS was 6.4 months and 95% CI was from 4.3 to 8.5 months. By contrast, in the cases where the level was less than 822 pg/ml, the median PFS was 2.2 months and 95% CI was from 1.6 to 2.8 months. In addition, in the cases where the VEGF-D level at day 8 after initiation of therapy was 822 pg/ml or higher, the median OS was 10.6 months and 95% CI was from 8.9 to 12.4 months. By contrast, in the cases where the level was less than 822 pg/ml, the median OS was 4.6 months and 95% CI was from 3.3 to 5.9 months.

Figure 6:
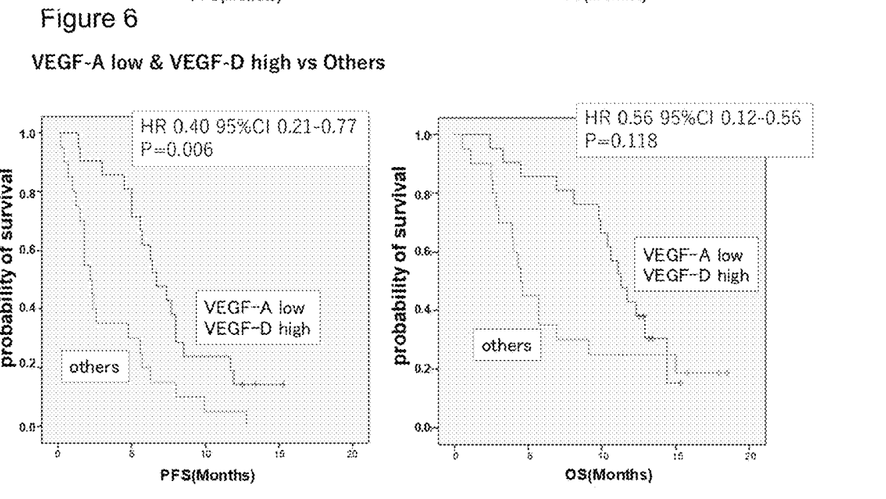
FIG. 6 is graphs indicating a PFS or OS correlation between a group with low VEGF-A levels and high VEGF-D levels and the other groups at day 8 after initiation of therapy with ramucirumab.

The above results show that if the VEGF-A level is low and the VEGF-D level is high at day 8 after initiation of therapy with ramucirumab, prognosis can be said to be good. Then, the prognosis was predicted by combining these two markers (FIG. 6). First, the cases were grouped, according to the VEGF-A and VEGF-D levels at day 8 after initiation of therapy, into 4 groups. The group, where the VEGF-A level was low, namely less than 456 pg/ml, and the VEGF-D level was high, namely 822 pg/ml or higher, was compared with the other 3 groups (FIG. 6).

In the patient group, where the VEGF-A level was low and the VEGF-D level was high (in the graphs, VEGF-A low, VEGF-D high), prognosis including both PFS and OS were clearly better than those of the other groups. In the group, where the VEGF-A level was low and the VEGF-D level was high, the median PFS was 6.7 months (95% CI: from 5.1 to 8.3 months). By contrast, in the other groups, the median PFS was 2.2 months (95% CI: from 1.1 to 3.3 months) and the p-value was 0.006, indicating a significant difference. Also, in the group, where the VEGF-A level was low and the VEGF-D level was high, the median OS was 11.3 months (95% CI: from 9.7 to 12.9 months). In the other groups, the median OS was 4.5 months (95% CI: from 3.8 to 5.2 months) and the p-value was 0.118.

Figure 7:
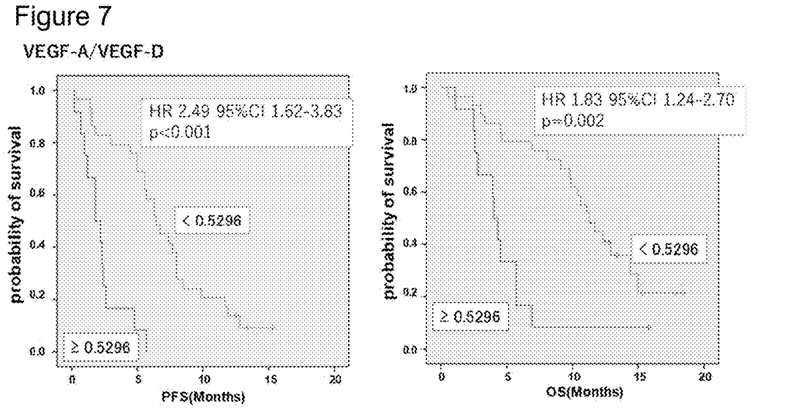
FIG. 7 is graphs indicating that a ratio of VEGF-A to VEGF-D is correlated with PFS or OS at day 8 after initiation of therapy with ramucirumab.

Further, how the VEGF-A/VEGF-D ratio was correlated with PFS or OS was analyzed. Then, a lower ratio (VEGF-A/VEGF-D) tended to reflect better prognosis. Thus, an optimal cut-off value was calculated, followed by further analysis. Here, the cut-off value was set to 0.5296 and PFS and OS were determined (FIG. 7). When the ratio was equal to or higher than the cut-off value 0.5296, the median PFS was 1.8 months (95% CI: from 0.7 to 2.9 months). When the ratio was less than 0.5296, the median PFS was 6.4 months (95% CI: from 5.1 to 7.7 months). When the ratio was equal to or higher than the cut-off value, the median OS was 4.0 months (95% CI: from 3.3 to 4.7 months). When the ratio was less than the cut-off value, the median OS was 11.3 months (95% CI: from 9.4 to 13.2 months). Accordingly, determination of the ratio between them allows for prediction of prognosis after therapy with and prediction of therapeutic effect of ramucirumab.

As described above, by measuring the VEGF-A and/or VEGF-D levels in blood samples from each patient during the early phase after initiation of therapy with ramucirumab, the therapeutic effect of and the prognosis after therapy with ramucirumab can be predicted. That is, use of these markers makes it possible to predict prognosis in the early phase after initiation of therapy with ramucirumab. This also makes it possible to select a different drug for patients from whom therapeutic benefit cannot be expected. The above-described cut-off value and other values are estimated values. The values may become more accurate after the analysis is conducted over a longer period in the future while the number of patients is increased.

A report shows that when an anti-VEGF-A antibody bevacizumab (trade name: Avastin) was used in combination with chemotherapy in gastric cancer therapy, PFS was prolonged but OS was not. Biomarker research in that study has reportedly demonstrated that the high baseline level of VEGF-A is a factor that indicates poor prognosis and predicts therapeutic efficacy of Avastin (Non Patent Literature 6).

In view of the above, there are reports about a predictive indicator for prognosis and a predictive indicator for therapeutic efficacy for an antibody drug against a ligand VEGF-A. However, there are no reports about any predictive indicator for prognosis or any predictive indicator for therapeutic efficacy for a medicine against a receptor VEGFR. The present study is the first to analyze a predictive indicator for prognosis and a predictive indicator for therapeutic efficacy for anti-VEGFR-2 antibody drug. This analysis has first demonstrated that a change in the level of VEGF-A during the early phase of therapy is useful as a predictive indicator for therapeutic effect of anti-VEGFR-2 antibody drug. In addition, VEGF-A has not previously known as a predictive indicator for therapeutic efficacy for anti-VEGFR-2 antibody drug, and this is a surprising effect. Specifically, after an anti-VEGF-A antibody Avastin was used, the concentration of VEGF-A decreased while the concentration increased when ramucirumab was used. This response is completely opposite and has been found to affect the therapeutic effect.

Figure 8:
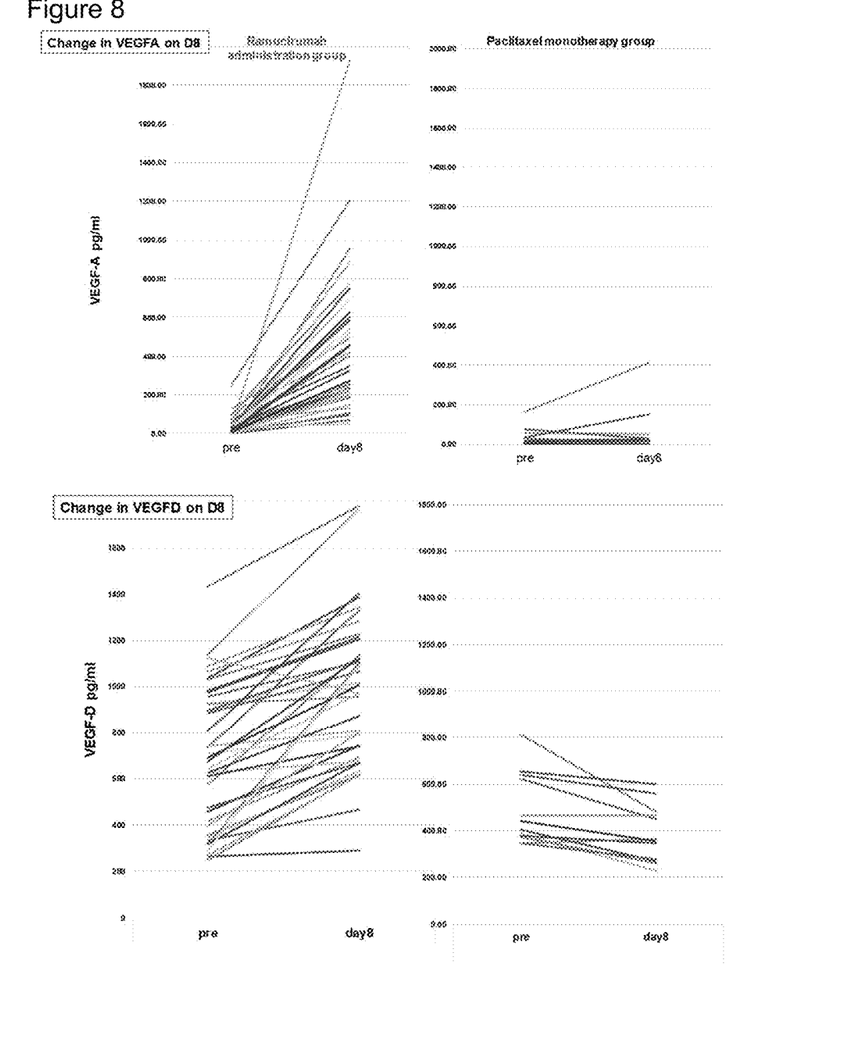
FIG. 8 is graphs showing changes in the level of VEGF-A or VEGF-D in the ramucirumab administration group or the paclitaxel single administration group between before initiation of therapy and day 8 after initiation of therapy.

Changes in the levels of VEGF-A and VEGF-D at day 8 after initiation of ramucirumab administration are specific to treatment using ramucirumab. Such changes cannot be seen when therapy using another chemotherapy is implemented. FIG. 8 shows changes in the blood concentration of VEGF-A (FIG. 8, upper panels) or VEGF-D (FIG. 8, the lower panels) between before administration and day 8 after initiation of the administration in the ramucirumab combination therapy patient group or the paclitaxel monotherapy patient group. In the ramucirumab administration group, the concentration of VEGF-A is found to have a clear increase at day 8 after initiation of administration when compared to the concentration before the initiation of administration. In addition, a significant change in the concentration of VEGF-D is unobserved in some patients, but a clear increase is recognized in many patients. By contrast, in the paclitaxel monotherapy group, no big changes in the concentration of VEGF-A or VEGF-D are observed.

Figure 9:
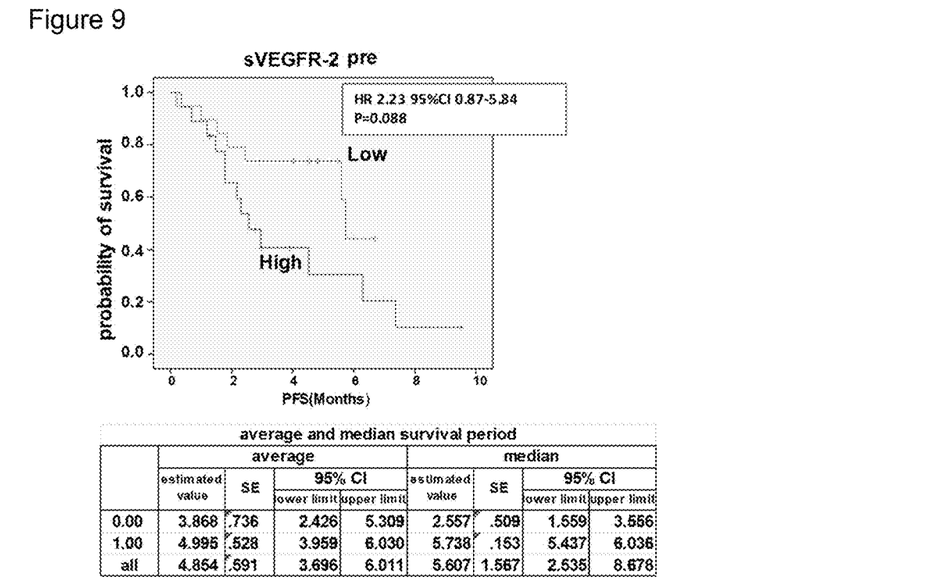
FIG. 9 is a graph and a table indicating that sVEGFR-2 is correlated with PFS.

The following illustrates markers that were associated in 39 cases described in Table 1. First, a relationship between sVEGFR-2 and PFS is described (FIG. 9). In the previous study, sVEGFR-2 was not reported as a predictive indicator for therapeutic efficacy (Non Patent Literature 3). However, in this analysis, as the baseline sVEGFR-2 becomes higher, PFS tends to be shorter. In the group where the level of sVEGFR-2 before therapy is lower than the median, PFS is 5.7 months. By contrast, in the group where the level is higher, PFS is 2.6 months. In view of subgroup analysis results of responders, sVEGFR-2 may serve as a predictive indicator for prognosis.

Figure 10:
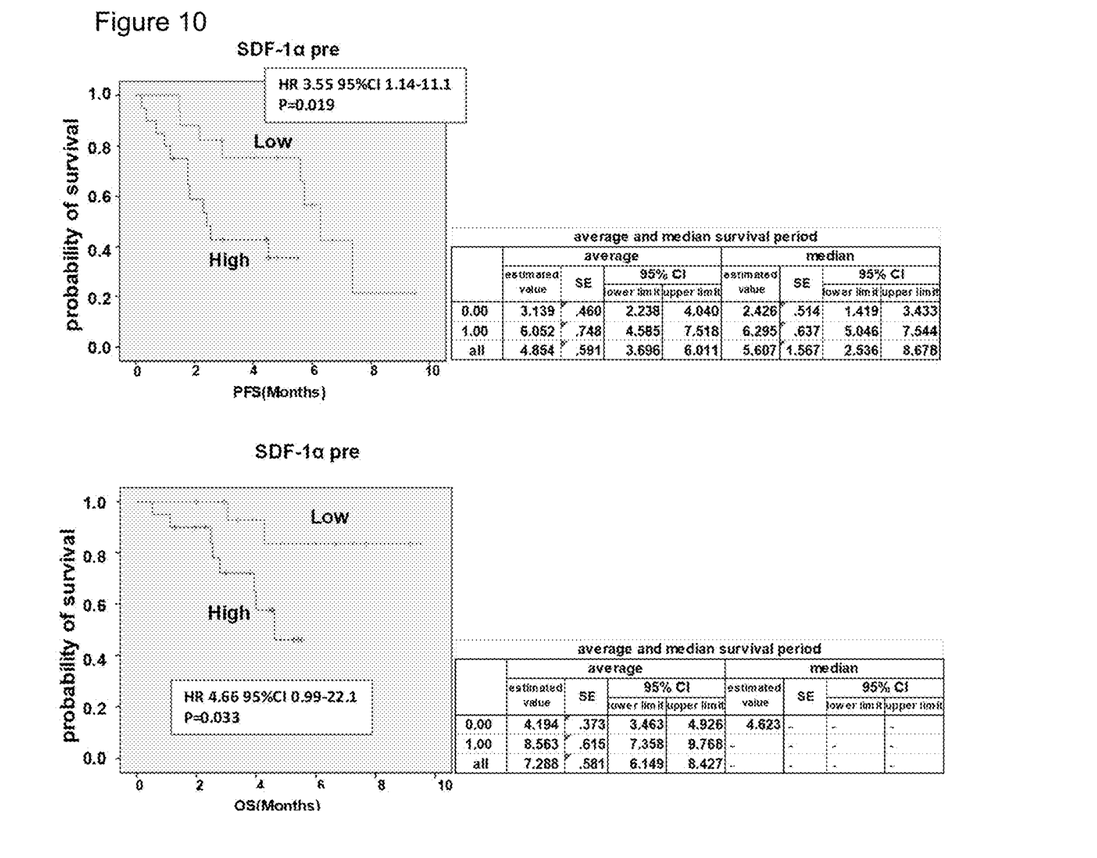
FIG. 10 is graphs and tables indicating that SDF-1α is correlated with PFS or OS.

The following shows the results of analyzing SDF-1α (FIG. 10). SDF-1α is a promising biomarker because from the early analysis stage including a small number of subjects, the therapeutic effect is found to vary depending on the baseline level. In view of the PFS analysis (FIG. 10, upper panels), in the patient group where the baseline level is lower than the median, PFS is 6.3 months. By contrast, in the patient group where the level is higher, PFS is 2.4 months and a significant difference is found. In addition, the same tendency is observed for OS. In the patient group where the baseline level is lower than the median, a higher therapeutic effect of ramucirumab is exerted (FIG. 10, the lower panels). SDF-1α is useful as a prognostic factor and is suggested, depending on the future analysis, to serve as a therapeutic effect predictor.

Figure 11:
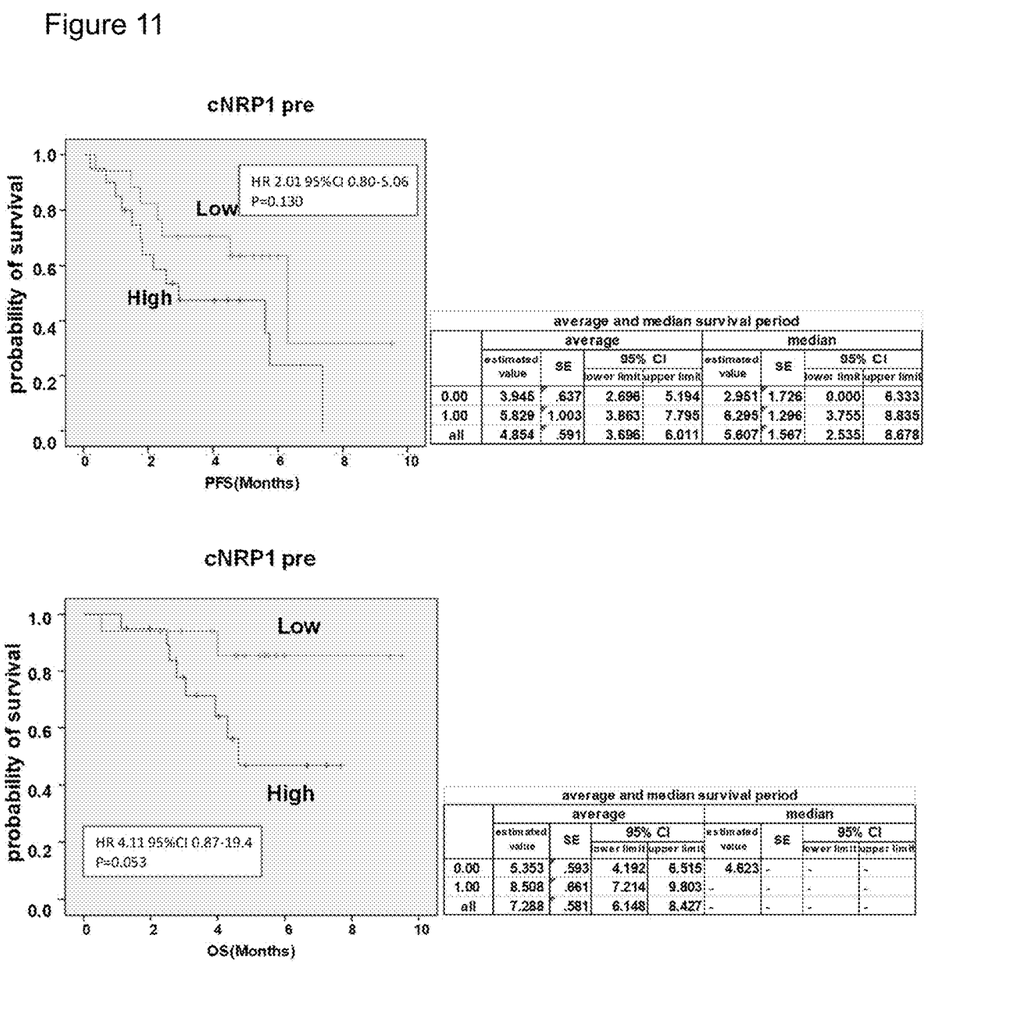
FIG. 11 is graphs and tables indicating that cNPR1 is correlated with PFS or OS.

Here, cNRP1 has been known to transduce an angiogenesis signal, participate in malignant transformation, and have a close relationship with VEGFR-2. So, cNRP1 should affect therapy. Currently, the results of this analysis have revealed that when the cNRP1 baseline is high, both PFS and OS tend to be shorter, but a significant difference is not observed. Even so, the future data and accumulated cases may specify cNRP1 as a predictive indicator for therapeutic efficacy and/or a predictive indicator for prognosis (FIG. 11).

VEGF, which participates in angiogenesis, has multiple family members. Then, its receptor VEGFR has also three members. Further, regarding action points of inhibitors, a plurality of mechanisms of action are present, including inhibition of a ligand, a receptor, or a tyrosine kinase downstream of the receptor. Accordingly, when a therapeutic strategy for controlling a VEGF system is planned, application of multiple agents may be considered. However, it is often currently unclear which agent is the best for a patient of interest. Whether or not an actually applied medical agent is relevant should be determined by biomarker(s) tested individually.

The present inventors have found biomarkers that can be used to choose a patient who responds to anti-VEGFR-2 antibody drug, in particular, ramucirumab. Consequently, therapy can be implemented while a therapy-responsive patient is chosen. At the same time, for patients from whom therapeutic benefit cannot be expected, alternative therapy can be selected without performing useless therapy.

In addition, according to the present invention, VEGF-A, VEGF-D, sVEGFR-2, SDF-1α, and cNRP1 in the blood can each be used as a biomarker that indicates responsiveness to therapy with an antibody drug for inhibiting VEGFR-2. Among them, the blood concentrations of VEGF-A and VEGF-D in the early phase after initiation of therapeutic, in particular, at day 8 are each a ramucirumab-specific response and are thus each considered to be a useful marker as a predictive indicator for prognosis and/or a predictive indicator for therapeutic efficacy. Hence, the present invention is applicable to prognosis prediction on not only ramucirumab but also anti-VEGFR-2 antibody drug and/or low-molecular-weight VEGFR-2 kinase inhibitors having substantially the same mechanism of action.

When the present invention is put into practice, patients to be treated can receive information about an option of a highly beneficial therapeutic protocol. On top of that, a preferable effect can be placed on proper drug usage and health economy.

In addition, in the future, analysis of prediction for therapeutic efficacy and prognostic markers may help develop a novel therapeutic protocol such as a protocol in combination with another drug. A group of patients who have received anti-VEGFR-2 antibody drug alone but do not receive sufficient therapeutic benefit should receive higher therapeutic benefit by testing pathological conditions, in which angiogenesis largely participates in cancer progression, and then by administrating another medical agent in combination.

FIGS. 3 and 4 demonstrate that ramucirumab is effective in the patient group where the VEGF-A level is low at D8, and there is no effect on the patients with a higher level. The markedly increased VEGF-A concentration at D8 is highly associated with resistance to therapy with ramucirumab. Thus, ramucirumab may be made effective in the ramucirumab-ineffective group with a higher VEGF-A level by substantially lowering the concentration of VEGF-A by using an VEGF-A-neutralizing antibody bevacizumab in combination. Future analysis on the effect of using ramucirumab in combination with bevacizumab is necessary. However, even in the group where ramucirumab has been administrated but does not produce an advantageous effect, the therapeutic effect may be exhibited.

The invention claimed is:

1. A test method for predicting therapeutic efficacy of and/or predicting prognosis in a gastric cancer patient for administration of ramucirumab as an anti-VEGFR-2 antibody drug, comprising:
   collecting blood samples from the gastric cancer patient before initiation of therapy with ramucirumab and in an early phase after initiation of therapy with ramucirumab, wherein the blood samples collected in the early phase after initiation of therapy with ramucirumab is collected between day 4 and day 10 after initiation of therapy with ramucirumab;
   measuring concentrations of VEGF-A in the blood samples collected from the patient before initiation of therapy and in the early phase after initiation of therapy;
   comparing the concentration of VEGF-A in the blood sample collected from the patient before initiation of therapy with the concentration of VEGF-A in the blood sample collected from the patient in the early phase after initiation of therapy; and
   determining the therapeutic efficacy and/or prognosis for administration is poor when a difference between the concentration of VEGF-A in the blood sample collected from the patient in the early phase after initiation of therapy and the concentration of VEGF-A in the blood sample collected from the patient before initiation of therapy is greater than a predetermined threshold difference.

2. The test method according to claim 1, wherein each of the blood samples is plasma or serum.

3. A test method for predicting therapeutic efficacy of and/or predicting prognosis in a gastric cancer patient for administration of ramucirumab as an anti-VEGFR-2 antibody drug, comprising:
   collecting blood samples from the gastric cancer patient in an early phase after initiation of therapy with ramucirumab, wherein the blood samples collected in the early phase after initiation of therapy with ramucirumab is collected between day 4 and day 10 after initiation of therapy with ramucirumab;
   measuring concentrations of VEGF-A and VEGF-D in the blood samples collected from the patient in the early phase after initiation of therapy;
   comparing the concentration of VEGF-A and VEGF-D in the blood sample collected from the patient in the early phase after initiation of therapy; and
   determining the therapeutic efficacy and/or prognosis for administration is good when a ratio of VEGF-A to VEGF-D in the blood sample collected from the patient in the early phase after initiation of therapy is lower than a predetermined threshold.

4. A test method for predicting therapeutic efficacy of and/or predicting prognosis in a gastric cancer patient for administration of ramucirumab as an anti-VEGFR-2 antibody drug, comprising:
   collecting blood samples from the gastric cancer patient before initiation of therapy with ramucirumab and in an early phase after initiation of therapy with ramucirumab, wherein the blood samples collected in the early phase after initiation of therapy with ramucirumab is collected between day 4 and day 10 after initiation of therapy with ramucirumab;
   measuring concentrations of VEGF-A in the blood samples collected from the patient before initiation of therapy and in the early phase after initiation of therapy;
   comparing the concentration of VEGF-A in the blood sample collected from the patient before initiation of therapy with the concentration of VEGF-A in the blood sample collected from the patient in the early phase after initiation of therapy; and
   determining the therapeutic efficacy and/or prognosis for administration is poor as a ratio of the concentration of VEGF-A in the blood sample collected from the patient in the early phase after initiation of therapy to the concentration of VEGF-A in the blood sample collected from the patient before initiation of therapy is greater than a predetermined threshold.

* * * * *